(12) United States Patent
O'Malley

(10) Patent No.: US 9,603,791 B2
(45) Date of Patent: *Mar. 28, 2017

(54) ORAL CARE PRODUCT FORMULATION

(71) Applicant: Paul O'Malley, Sylmar, CA (US)

(72) Inventor: Paul O'Malley, Sylmar, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/198,221

(22) Filed: Jun. 30, 2016

(65) Prior Publication Data

US 2016/0310407 A1   Oct. 27, 2016

Related U.S. Application Data

(63) Continuation of application No. 14/340,989, filed on Jul. 25, 2014, now Pat. No. 9,403,181.

(60) Provisional application No. 61/859,135, filed on Jul. 26, 2013.

(51) Int. Cl.

| | | |
|---|---|---|
| A61K 8/99 | (2006.01) | |
| A61K 33/30 | (2006.01) | |
| A61K 33/42 | (2006.01) | |
| A61K 8/02 | (2006.01) | |
| A61K 9/68 | (2006.01) | |
| A61K 8/27 | (2006.01) | |
| A61K 8/24 | (2006.01) | |
| A61K 9/00 | (2006.01) | |
| A61Q 11/00 | (2006.01) | |
| B05C 17/005 | (2006.01) | |
| A61K 8/34 | (2006.01) | |
| A61K 8/365 | (2006.01) | |
| A61K 8/66 | (2006.01) | |
| A61K 8/92 | (2006.01) | |
| A61K 8/97 | (2017.01) | |
| A61K 8/19 | (2006.01) | |
| A61K 8/22 | (2006.01) | |
| A61K 35/744 | (2015.01) | |
| A61K 35/747 | (2015.01) | |
| A47K 5/12 | (2006.01) | |
| A61K 35/00 | (2006.01) | |

(52) U.S. Cl.
CPC .............. *A61K 8/99* (2013.01); *A61K 8/0204* (2013.01); *A61K 8/19* (2013.01); *A61K 8/22* (2013.01); *A61K 8/24* (2013.01); *A61K 8/27* (2013.01); *A61K 8/345* (2013.01); *A61K 8/365* (2013.01); *A61K 8/66* (2013.01); *A61K 8/922* (2013.01); *A61K 8/97* (2013.01); *A61K 9/0056* (2013.01); *A61K 9/0058* (2013.01); *A61K 33/30* (2013.01); *A61K 33/42* (2013.01); *A61K 35/744* (2013.01); *A61K 35/747* (2013.01); *A61Q 11/00* (2013.01); *B05C 17/00569* (2013.01); *A47K 5/1205* (2013.01); *A61K 2035/115* (2013.01)

(58) Field of Classification Search
USPC .................................... 424/48, 49, 50, 93.46
See application file for complete search history.

(56) References Cited

U.S. PATENT DOCUMENTS

| | | | | |
|---|---|---|---|---|
| 2009/0117056 A1* | 5/2009 | Hodal, Jr. | ............... | A23L 1/097 424/48 |
| 2012/0251512 A1* | 10/2012 | Farmer | ................. | A23L 1/3014 424/93.46 |
| 2013/0344010 A1* | 12/2013 | Pompejus | ............. | A23L 1/3014 424/50 |
| 2015/0030546 A1* | 1/2015 | O'Malley | ......... | B05C 17/00569 424/49 |

* cited by examiner

*Primary Examiner* — Walter Webb
(74) *Attorney, Agent, or Firm* — Hackler Daghighian Martino & Novak

(57) ABSTRACT

A probiotic formulation includes the following: *lactobacillus acidophilus* comprising 15.0% to 40.0% per mass of the probiotic formulation; *lactobacillus reuteri* comprising 5.0% to 20.0% per mass of the probiotic formulation; *lactobacillus salivarius* comprising 5.0% to 20.0% per mass of the probiotic formulation; *lactobacillus paracasei* comprising 5.0% to 20.0% per mass of the probiotic formulation; *streptococcus* thermophiles comprising 5.0% to 20.0% per mass of the probiotic formulation; *streptococcus salivarius* BLIS K-12 comprising 5.0% to 30.0% per mass of the probiotic formulation; *streptococcus salivarius* BLIS M-18 comprising 5.0% to 30.0% per mass of the probiotic formulation; zinc oxide comprising 0.2% to 5.0% per mass of the probiotic formulation; hydroxyapatite comprising 0.1% to 25.0% per mass of the probiotic formulation; and dicalcium phosphate comprising 0.1% to 5.0% per mass of the probiotic formulation. The probiotic formulation may be formed into a lozenge or a gum.

18 Claims, 1 Drawing Sheet

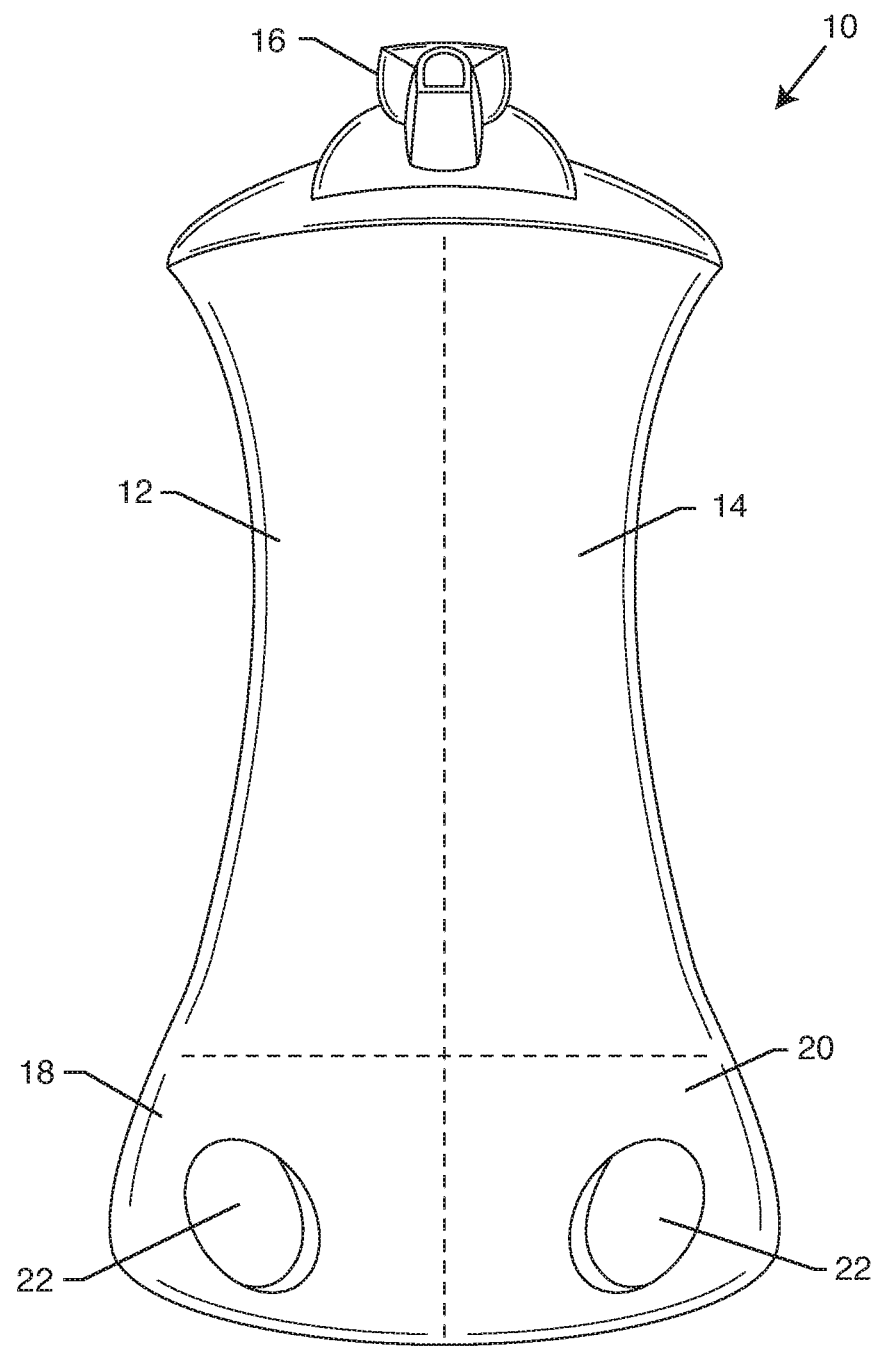

9,603,791 B2

ORAL CARE PRODUCT FORMULATION

CROSS-REFERENCE TO RELATED APPLICATIONS

This application is a continuation application which claims priority to application Ser. No. 14/340,989 filed on Jul. 25, 2014, which itself claims priority to provisional application 61/859,135 filed on Jul. 26, 2013, the contents of which all applications are fully incorporated herein with these references.

DESCRIPTION

Field of the Invention

The present invention generally relates to oral care. More particularly, the present invention relates to a formulation of a product that cleans, whitens, kills germs and bacteria, freshens breath, reduces tooth sensitivity, reduces gingivitis, reverses early holes in teeth, and leaves the mouth with a feel good factor that can be incorporated into toothpaste, mouthwash, dental sprays, lozenges, gum, floss, toothpicks, solution for water pik/irrigators, impregnated into the bristles of disposable tooth brushes and other dental products.

BACKGROUND OF THE INVENTION

The practice of cleaning the human mouth and human teeth is practiced throughout the world on a daily basis. This is because many people want to kill and destroy harmful oral microorganisms while also having white and healthy looking teeth while also reducing bad breath.

The most common method of cleaning is tooth brushing. Brushing ones teeth has been a dental care concept for many years, known to have been observed in the ancient Egyptians. The act of tooth brushing normally consists of two tools: a toothbrush and toothpaste. A toothbrush consists of a handle which has fiber bristles on one end, as this brush is used to scrub the teeth. Toothpaste is a gel paste often applied to the toothbrush to enhance oral hygiene. Toothpastes have also been known to have another usage, which is to beautify teeth.

Many people have also used various cleaning liquids designed to be used within a person's mouth. These liquids are mouthwashes, mouth rinses, oral rinses or mouth baths which are held in the mouth passively or swilled around the mouth by contraction of the perioral muscles and/or movement of the head, and may be gargled, where the head is tilted back and the liquid bubbled at the back of the mouth. Usually mouthwashes are an antiseptic solution intended to reduce the microbial load in the oral cavity, although other mouthwashes might be given for other reasons such as for their analgesic, anti-inflammatory or anti-fungal action.

The most common use of mouthwash is commercial antiseptics which are used at home as part of an oral hygiene routine. Some manufacturers of mouthwash claim that antiseptic and anti-plaque mouth rinse kill the bacterial plaque which causes cavities, gingivitis, and bad breath. Anti-cavity mouth rinse uses fluoride to protect against tooth decay. It is, however, generally agreed that the use of mouthwash does not eliminate the need for both brushing and flossing.

There are other forms of cleaning as well that involve flossing or going to a professional dentist for a thorough cleaning. As can be seen, there is always a need for improved methods and compositions that better clean and protect one's teeth. The present invention fulfills these needs and provides other related advantages.

SUMMARY OF THE INVENTION

An exemplary embodiment of a two-part oral care system, comprises a first vessel containing an oxidative composition, the oxidative composition having a pH less than 7.5 and a second vessel containing a reductant composition, the reductant composition having a pH greater than 7. The first and second vessels isolate the oxidative and reductant compositions from reacting with one another during storage. The first and second vessels can dispense the oxidative and reductant compositions for combining to result in a final composition for use. The oxidative composition comprises an ozonated oil comprising 0.01% to 5.0% per mass of the final composition and an oxidant comprising 0.01% to 2.0% per mass of the final composition. The reductant composition comprises an aloe gel or aloe vera comprising 0.01% to 25.0% per mass of the final composition, a xylitol comprising 0.1% to 60.0% per mass of the final composition, a ferrous sulfate comprising 0.0001% to 0.1% per mass of the final composition, a sodium bicarbonate comprising 0.01%-6.0% per mass of the final composition, a calcium carbonate comprising 1.0%-40.0% per mass of the final composition, a zinc gluconate comprising 0.01%-3.0% per mass of the final composition, a salt comprising 0.01%-3.0% per mass of the final composition, a bromelain comprising 0.01%-3.0% per mass of the final composition, a papain comprising 0.01%-3.0% per mass of the final composition and at least one essential oil comprising 1.0 to 3.5% per mass of the final composition. The oxidative composition and the reductant composition comprise 100.0% per mass of the final composition.

In other exemplary embodiments the ozonated oil may comprise olive oil, grapeseed oil, hempseed oil or avocado oil wherein the oil is infused with ozone. The oxidant may comprise hydrogen peroxide or chlorine dioxide. The oxidative composition may further comprises calcium citrate comprising 0.01% to 3.0% per mass of the final composition.

The salt may comprise a sea salt. The sea salt may comprise a kosher flake sea salt, a fine sonoma sea salt or a pink himalayan sea salt.

A surfactant may be added to either the oxidative composition or the reductant composition, the surfactant comprising 0.5% to 3.0% per mass of the final composition. The surfactant may comprise sodium coco sulfate or sodium decylglucoside.

The reductant composition may comprise a nano particle silver water comprising 0.1% to 10.0% per mass of the final composition.

The reductant composition comprises a hydroxyapatite comprising 0.1% to 4.0% per mass of the final composition.

The oxidative composition may comprise a pH equal to or between 6.3 to 7.5.

The at least one essential oil may be selected from the group consisting of eucalyptol, mentol and thymol.

The first vessel may be permanently attached to the second vessel.

The present invention may also include a probiotic lozenge to be used after the final composition. The probiotic lozenge may comprise *lactobacillus acidophilus* comprising 15.0% to 40.0% per mass of the probiotic lozenge, *lactobacillus reuteri* comprising 5.0% to 20.0% per mass of the probiotic lozenge, *lactobacillus salivarius* comprising 5.0% to 20.0% per mass of the probiotic lozenge, *lactobacillus*

*paracasei* comprising 5.0% to 20.0% per mass of the probiotic lozenge, *streptococcus* thermophiles comprising 5.0% to 20.0% per mass of the probiotic lozenge, *streptococcus salivarius* BLIS K-12 comprising 5.0% to 30.0% per mass of the probiotic lozenge, *streptococcus salivarius* BLIS M-18 comprising 5.0% to 30.0% per mass of the probiotic lozenge, zinc oxide comprising 0.2% to 5.0% per mass of the probiotic lozenge, hydroxyapatite comprising 0.1% to 25.0% per mass of the probiotic lozenge and dicalcium phosphate comprising 0.1% to 5.0% per mass of the probiotic lozenge. The probiotic lozenge may further include *lactobacillus brevis* comprising 5.0% to 20.0% per mass of the probiotic lozenge.

The first vessel may be permanently attached to the second vessel, and further including a third vessel which may be attached to either the first or second vessel, where the third vessel contains a plurality of the probiotic lozenges.

Other features and advantages of the present invention will become apparent from the following more detailed description, when taken in conjunction with the accompanying drawings, which illustrate, by way of example, the principles of the invention.

BRIEF DESCRIPTION OF THE DRAWINGS

The accompanying drawings illustrate the invention. In such drawings:

FIG. 1 illustrates a front view of an exemplary embodiment of the product container of the present invention.

DETAILED DESCRIPTION OF THE PREFERRED EMBODIMENTS

The present invention concerns cleaning one's teeth and the general health of one's mouth as well as improving the feel good factor. One of the embodiments of the present invention is a toothpaste or other dental related product that includes ozonated oils and/or ozonides combined with other oxidants such as hydrogen peroxide or hydrogen peroxide producing agents or chlorine dioxide.

Ozone can be infused into oil which acts as a carrier and can produce ozonides. For instance, olive oil can be infused with ozone. Other oils may be used as well, as for example grape seed oil, hempseed oil or avocado oil. Ozonides are formed which then are active in the product. The oil helps to trap the ozone for longer periods of time as compared to infusing the ozone into water or other carriers.

The present formulation can be combined or integrated into toothpaste, mouth spray, mouthwash, lozenges, gum, floss, toothpicks, solution for water pik/irrigators, impregnated into the bristles of disposable and regular tooth brushes, and any other various dental tools.

In a further embodiment of the present invention the final composition intended for use can be separated into two different component parts that are only combined right before use. This means that a first composition can be an oxidative composition and the second composition can be a reductant composition. Separating the compositions improves the effectiveness of the final product as mixing all components may dilute or render their cleaning and health effects as ineffective or less effective. For instance the toothpaste, spray, mouthwash or irrigation solution can be combined right before use such that each individual component is not rendered ineffective over the storage period which can be weeks or months or even years.

The first component of the present invention can include the ozonated oils and the oxidants, such as hydrogen peroxide or hydrogen peroxide producing agents or chlorine dioxide. The first component is generally acidic, having a pH less than 7.5. More specifically, the pH would be equal to or between 6.3 to 7.5. The first components are generally acidic in order to increase the shelf life of the peroxide and other ingredients. The first component may also include calcium and other fillers. More specifically, the oxidative composition may include calcium citrate.

In one embodiment of the present invention, the oxidative composition may comprises an ozonated oil comprising 0.01% to 5.0% per mass of the final composition and an oxidant comprising 0.01% to 2.0% per mass of the final composition. Furthermore, the oxidative composition may further comprise calcium citrate comprising 0.01% to 3.0% per mass of the final composition.

The second/reductant composition of the present invention is generally basic (alkaline), having a pH generally above 7. For instance, the second component may include sodium hydroxide or other substances that creates a pH above 7. Then, when the first composition and the second composition are mixed, the resulting combination may be slightly basic (alkaline) with a pH of around 7.1.

In one embodiment of the present invention, the reductant composition includes an aloe gel or aloe vera comprising 0.01% to 25.0% per mass of the final composition, a xylitol comprising 0.1% to 60.0% per mass of the final composition, a ferrous sulfate comprising 0.0001% to 0.1% per mass of the final composition, a sodium bicarbonate comprising 0.01%-6.0% per mass of the final composition, a calcium carbonate comprising 1.0%-40.0% per mass of the final composition, a zinc gluconate comprising 0.01%-3.0% per mass of the final composition, a salt comprising 0.01%-3.0% per mass of the final composition, a bromelain comprising 0.01%-3.0% per mass of the final composition, a papain comprising 0.01% -3.0% per mass of the final composition and at least one essential oil comprising 1.0 to 3.5% per mass of the final composition. Together the oxidative composition and the reductant composition comprise 100.0% per mass of the final composition.

In other exemplary embodiments, the salt used may be a sea salt. For example the sea salt may be a kosher flake sea salt, a fine sonoma sea salt or a pink himalayan sea salt.

A surfactant may be added to either the oxidative composition or the reductant composition. The surfactant may comprise 0.5% to 3.0% per mass of the final composition. More specifically, the surfactant may be a sodium coco sulfate or a sodium decylglucoside.

The reductant composition may include a nano particle silver water comprising 0.1% to 10.0% per mass of the final composition.

The reductant composition may include a hydroxyapatite comprising 0.1 to 4.0% per mass of the final composition.

The at least one essential oil may be either eucalyptol, mentol or thymol.

The first vessel may be permanently attached to the second vessel. This would aid the consumer/user in correctly utilizing the product as both vessels would be attached and not separated or lost from one another.

In another exemplary embodiment of the present invention, the system may further including a probiotic lozenge to be used after the final composition. The final composition kills the bad bacteria and germs while then the lozenge would apply good germs and bacteria. The lozenge may be stored within a third vessel that is also attached to the first and second vessels. This would help the consumer/user to remind them to use the lozenge after the use of the final composition.

In an exemplary embodiment disclosed in the provisional application, the probiotic lozenge includes a plurality of probiotics, the plurality of priobotics including *streptococcus salivarius* (BLIS K-12) comprising about 25% per mass of the probiotic lozenge, *S thermophilus* comprising about 25% per mass of the probiotic lozenge, *L paracasei* comprising about 20% per mass of the probiotic lozenge, *L salivarius* comprising about 20% per mass of the probiotic lozenge and *L reuteri* comprising about 10% per mass of the probiotic lozenge wherein the plurality of probiotics comprise 100.0% per mass of the probiotic lozenge.

In another exemplary embodiment disclosed herein which is another embodiment, the probiotic lozenge includes a plurality of probiotics and ingredients, the plurality of priobotics and ingredients including: (i.) *lactobacillus acidophilus* comprising 15.0% to 40.0% per mass of the probiotic lozenge; (ii.) *lactobacillus reuteri* comprising 5.0% to 20.0% per mass of the probiotic lozenge; (iii.) *lactobacillus salivarius* comprising 5.0% to 20.0% per mass of the probiotic lozenge; (iv.) *lactobacillus paracasei* comprising 5.0% to 20.0% per mass of the probiotic lozenge; (v.) *streptococcus* thermophiles comprising 5.0% to 20.0% per mass of the probiotic lozenge; (vi.) *streptococcus salivarius* BLIS K-12 comprising 5.0% to 30.0% per mass of the probiotic lozenge; (vii.) *streptococcus salivarius* BLIS M-18 comprising 5.0% to 30.0% per mass of the probiotic lozenge; (viii.) zinc oxide comprising 0.2% to 5.0% per mass of the probiotic lozenge; (ix.) hydroxyapatite comprising 0.1% to 25.0% per mass of the probiotic lozenge; and (x.) dicalcium phosphate comprising 0.1% to 5.0% per mass of the probiotic lozenge. Other excipients may also be added to the lozenge such that all of the ingredients and the excipients comprise 100% of the probiotic lozenge.

None in the prior art have realized that the *lactobacilli* can only colonize the teeth when the *streptococci* will be present to produce the sticky matrix that allows the *lactobacilli* to prosper. A balance is necessary where too much of one or other will lead to reduced effectiveness. There is the synergy between the present invention's strep strains combined with the *lactobacilli*. Therefore, the present inventions unique combination of the streps and *lactobacilli* can uniquely replace the pathogenic streps and *lactobacilli*.

*Streptococcus salivarius* (BLIS K-12) is one of the most numerous beneficial bacteria found in the mouth of healthy individuals. However, only a small percent of people have *S. salivarius* with BLIS K-12 activity. The K-12 strain was originally discovered as scientists tracked the oral bacteria of a healthy child, who did not develop sore throats for several years. Scientists found that this particular K-12 strain of *S. salivarius* secretes powerful antimicrobial molecules called BLIS (Bacteriocin-Like-Inhibitory-Substances) with the ability to inhibit harmful bacteria such as the bacteria responsible for bad breath, sore throat and other upper respiratory infections. This is an advanced probiotic strain for the oral cavity and upper respiratory tract. It is a specific strain of *S. salivarius* with actions to help provide a natural long-term breath support while boosting our immune system's natural defenses.

*Streptococcus salivarius* (BLIS M-18) is among the most important and beneficial bacteria of the mouth and appears in the mouth of newborns within hours after birth. It is also one of the most dominant bacteria found in the oral cavity and substantial research links *S. salivarius* with good oral health. However, some *S. salivarius* are more beneficial than others and BLIS M18 is one of those highly beneficial bacteria. Unfortunately, most people do not have sufficient *S. salivarius* with BLIS M18 activity to promote oral and dental health. Not all strains of *S. salivarius* act equally to inhibit oral and dental microbes. BLIS M18 is a naturally occurring strain that In vitro studies have shown is especially potent at inhibiting *Streptococcus mutans* (*S. mutans*). *S. mutans* is a harmful oral bacteria considered a leading causative of dental tooth decay.

*Lactobacillus Acidophilus* is a lactic acid bacterium with the ability to produce hydrogen peroxide. This may be one of the reasons it is effective in inhibiting pathogenic microorganisms from inhabiting and growing in the body. *L. acidophilus* produces natural antibacterials called lactocidin and acidophilin. These enhance resistance to pathogens. It is known to have an effective antimicrobial effect against *Staphylococcus aureus, Salmonella, E. coli Rotavirus* and *Candida albicans*. It is naturally found in humans and animals and colonizes well in the human digestive tract. *L. acidophilus* is one of the most well-known probiotics due to its natural presence in yogurt. It takes up residence in the small intestine, vagina, urethra and cervix. It aids in the production of niacin, folic acid and pyridoxine, three B vitamins. It may lower serum cholesterol and has been found to be effective against antibiotic-associated diarrhea. It also appears to offer health benefits to people suffering from atopic disease, including dermatitis. Resistant to stomach acids and bile salts, this probiotic is a good candidate for effectively reaching the intestines after oral consumption. The first studies of the use of probiotics for enhancing oral health were for the treatment of periodontal inflammation. Patients with various periodontal diseases, gingivitis, periodontitis, and pregnancy gingivitis were locally treated with a culture supernatant of a *L. acidophilus* strain. Significant recovery was reported for almost every patient.

*Lactobacillus salivarius* helps normalize the intestinal flora in those suffering from chronic bowel conditions such as irritable bowel syndrome. It is a lactic acid bacterium. *L. salivarius* may be an effective inhibitor of the bacteria *H. pylori,* a bacterium associated with the formation of ulcers in the stomach. *L. salivarius* also appears to reduce flatulence. Use of tablets containing *L. salivarius* has been shown to decrease gingival pocket depth, particularly in high-risk groups such as smokers, and also affect the number of periodontopathogens in plaque.

*Lactobacillus paracasei* is a strain naturally found in fermented products, yogurt and natural dairy products like raw milk. You will not find this friendly bacterium in pasteurized milk because the manufacturing process actually kills all the good and bad bacteria in addition to other nutrients. Research shows that *Lactobacillus paracasei* improves digestion and immune function by fighting off bad bacteria. These healthy bacteria can also help the body in many other ways. For instance, this strain of flora helps to calm digestive upsets, assists other strains of bacterium, as well as improves the absorption of nutrients and lipids in the gut. This strain has been demonstrated to inhibit the growth of many pathogenic microbes such as *Streptococcus mutans* (*S. mutans*). In fact, in a clinical trial this strain was shown to significantly reduce *S. mutans* between the 2nd and 3rd weeks of administration. Thus, a two week period of medication via oral administration may be best for *L. paracasei* to be effective.

*Lactobacillus reuteri* is one of the most studied species as it offers two unique features. *L. reuteri* produces reuterin, an antimicrobial substance that has been found to be effective against many pathogenic microbes including *Rotavirus. L. reuteri* is a gram-positive, lactic acid bacterium that was originally isolated from human breast milk and is also found in most mammals' intestines. Effective in infants and children suffering from *Rotavirus* infections, *L. reuteri* can reduce the severity and duration of diarrhea. It is also effective against antibiotic-associated diarrhea and traveler's diarrhea. It may also be effective against diarrhea caused by *Clostridium difficile*. Its antimicrobial actions also appear to eradicate *Helicobacter pylori*, the bacteria associated with ulcer formation in the stomach. *L. reuteri* has beneficial effects on the immune system and appears to be useful in those with atopic diseases. There has been significant interest in using probiotics in treatment of periodontal disease. This probiotic strain has improved gingival health, as measured by decreased gum bleeding and has also been shown to decrease levels of pro-inflammatory cytokines in Gingival Crevicular Fluid.

*Streptococcus* thermophiles is a sub-species of *Streptococcus Salivarius* and may provide many of the same benefits of *S. salivarius* strains. This strain is a gram-positive species of bacterium, which colonizes in the mouth and upper respiratory tract of human a few hours after birth and are normal inhabitants of the oral cavity, oropharynx and upper respiratory tract.

Referring back to the final composition of the two-part oral care system, other exemplary embodiments may include further beneficial ingredients. For example, another important ingredient in the present invention may also include Vitamin E. Vitamin E and the ozonides are used to turn on the natural healing properties and will reduce inflammation.

Another important aspect of the present invention is including proteolyic enzymes. The proteolyic enzymes also need to be on the other side to the oxidants as the oxidants would degrade them. In other words, the proteolyic enzymes should be in the second/reductant composition.

Furthermore, various detergents may be added to the present invention. If any detergents are used in the present invention, the detergents should also be stored separate from the oxidants and placed in the second/reductant composition. For example, decyl glucoside may be added where it comprises 0.2-3.0% per mass of the final composition.

Other exemplary embodiments may add hydroxyapatite where it comprises 0.01% to 20.0% per mass of the final composition.

Other exemplary embodiments may add 0.01-10 mgs of zinc to the final composition.

Other exemplary embodiments may add bioactive glass to the final composition.

Other exemplary embodiments may add muco-adhesive tablets to slow the delivery/release of the products in the mouth.

Other exemplary embodiments may add to the reductant composition nanoparticles of silver (Ag), cuprous oxide (Cu(2)O), cupric oxide (CuO), zinc oxide (ZnO) or titanium dioxide (TiO(2)).

Other exemplary embodiments may add bacteriophages to the final composition.

Other exemplary embodiments may add silver water comprising 200 parts per million in purified water to the final composition.

Various extracts may be added to the reductant composition such as green tea extract, spinosa fruit extract, horse chestnut seed and grapefruit seed extract.

One exemplary embodiment of the present invention may include, per percentage mass of the final composition, the various ingredients listed below. The reductant composition may include: iron at about 0.0001%, Xylitol at 30.205%, Bentonite at 1.20%, Bamboo Scrumbami 200/500 at 0.20%, Sea Salt (Kosher Flake, Fine Sonoma) at 0.64%, Peppermint Wow (3251359831) (make sure to blend prior to addition) at 2.00%, Super Sweet Blend #1 (3251359841) (make sure to blend powder prior to addition) at 0.27%, 40% Water Soluble Coenzyme Q 10 at 0.10%, Aloe Gel at 17.79%, Magnesium chloride at 0.1%, Vitamin E at 0.1%, Proteolytic enzymes (probably papain from papaya fruit and Bromelain from pineapple) at 0.2% of each, *Prunus Spinosa* (Blackthorn) Fruit Juice at 0.1%, *Krameria Triandra* (Ratanhia) Root Extract at 0.1%, *Krameria Triandra* (Ratanhia) Root Extract at 0.1%, *Aesculus Hippocastanum* (Horse Chestnut) Bark Extract at 0.1%, *Arum Maculatum* Root Extract at 0.1%, *Simmondsia Chinensis* (Jojoba) Seed Oil at 0.1%, Esculin at 0.1%, Limonene at 0.1%, Linalool at 0.1%, eucalyptus oil at 0.1%, myrrh at 0.1%, plant extract (strawberry extract) at 0.1%, Green tea extract at 0.1%, Tea tree oil at 0.1%, grapefruit seed extract at 0.1%. The oxidation composition may include: sodium mono fluoride phosphate to deliver fluoride @ 1450 ppm, hydrogen peroxide at 0.2%, ozonated oil (probably Ozonated Olive oil) at 0.2%, Ascorbic Acid (USP/FCC) at 0.10%, TICorganic® Guar Gum 3500 F Powder at 0.77%, Deionized Water at 14.56%, Vicality Light (Calcium Carbonate) at 28.92, Sodium Bicarbonate at 0.2%, Zinc Gluconate at 0.20% and hydroxylapatite at 0.1%.

It was very difficult to figure out how to make the present invention when it was formed into a toothpaste. The following method overcomes manufacturing problems. Regarding the reductant composition, the ingredients are mixed within a Silverson® mixer device or other equivalent mixer suitable for mixing the ingredients. The surfactant is added second to last in the mixing process. Than the essential oils are added last. At the very end a powder/liquid mix of natural flavor may also be added. This means that most of the ingredients are mixed first, then the surfactant, then the essential oils and then the natural flavors.

Now with regards to the oxidative composition, the ingredients are mixed within a Silverson® mixer or other equivalent mixer. This means that the water is added to the ingredients and thoroughly mixed. Then surfactant is added second to last. At the very last the ozonated oils and guar gum and calcium carbonate are added. However, the ozonated oils and guar gum and calcium carbonate are premixed together before being added to the rest of the ingredients. Then this ozonated oil, guar gum, calcium carbonate mixtures can be added to the rest of the oxidative ingredients. This method of manufacture is an exemplary embodiment as it does not ruin or destroy the effectiveness of the various ingredients.

An advantage of the present invention is that all the ingredients are all natural. Furthermore, the present invention is substantially free of glycerin, or about 98 percent free of glycerin.

Another important aspect of the present invention is that the component without the oxidants can contain elements like iron in order to active the hydrogen peroxide. The reaction of iron and hydrogen peroxide has been described as the Fenton reaction and there are several other elements which can also activate the hydrogen peroxide for which the present invention can also include.

One embodiment of the present invention as disclosed in the provisional application may comprise the following formulation below in percentages of mass of the final composition: Xylitol at about 33.25% with a possible range at or between 0.1% -60%, TICorganic® Guar Gum 3500 F Powder at about 0.77% with a possible range at or between 0.1%-3%, Bentonite at about 1.20% with a possible range at or between 0.1%-3%, Zinc Gluconate at about 0.20% with a possible range at or between 0.01% -3%, Ascorbic Acid, USP/FCC at about 0.10% with a possible range at or between 0.001%-3%, Vicality Light (Calcium Carbonate) at about 28.92% with a possible range at or between 1%-40%, Bamboo Scrumbami 200/500 at about 0.20% with a possible range at or between 0.01%-3%, Sea Salt (Kosher Flake, Fine Sonoma) at about 0.64% with a possible range at or between 0.01%-3%, Peppermint Wow (3251359831) (note to make sure to blend prior to addition) at about 2.00% with a possible range at or between 0.01%-5%, Deionized Water at about 14.56% with a possible range at or between 0.10%-30%, Super Sweet Blend #1 (3251359841) (note to make sure to blend powder prior to addition) with a possible range at or between 0.27% to 4.0%, Water Soluble Coenzyme Q 10 at about 0.10% with a possible range at or between 0.01%-3% and Aloe Gel at about 17.79% with a possible range at or between 0.01% -25% where all of these components equal to a total of 100% of the final composition.

Another embodiment of the present invention as disclosed in the provisional application may include the following ingredients: Calcium citrate with a possible range at or between 0.01%-3%, Zinc with a possible range at or between 0.01%-3% (Note that zinc is not needed if zinc gluconate is already used as shown above), Magnesium chloride with a possible range at or between 0.01%-3%, Baking Soda with a possible range at or between 0.01%-6%, Peroxide with a possible range at or between 0.01%-2%, Aloe Vera with a possible range at or between 0.01%-9%; (Note that Aloe Vera is not needed if Aloe Gel is already used., Vitamin E with a possible range at or between 0.01%-3%, Ozonated oil (probably Ozonated Olive oil) with a possible range at or between 0.01%-5%, Proteoltic enzymes (Papain with a possible range at or between 0.01%-3% from papaya fruit and Bromelain Range with a possible range at or between 0.01%-3% from pineapple), Sodium Bicarbonate with a possible range at or between 0.01%-6%, *Mentha Piperita* (Peppermint) Oil with a possible range at or between 0.01%-6%, *Prunus Spinosa* (Blackthorn) Fruit Juice with a possible range at or between 0.01%-6%, *Commiphora Myrrha* (Myrrh) Extract with a possible range at or between 0.01%-6%, *Krameria Triandra* (Ratanhia) Root Extract with a possible range at or between 0.01%-6%, *Aesculus Hippocastanum* (Horse Chestnut) Bark Extract with a possible range at or between 0.01%-6%, *Arum Maculatum* Root Extract with a possible range at or between 0.01%-6%, Sodium Chloride (Salt) with a possible range at or between 0.01%-6%, Cyanopsis Tetragonoloba (Guar) Gum with a possible range at or between 0.01%-6%, *Simmondsia Chinensis* (Jojoba) Seed Oil with a possible range at or between 0.01% -6%, Esculin with a possible range at or between 0.01%-6%, Limonene with a possible range at or between 0.01%-6%, Linalool with a possible range at or between 0.01% -6%, Eucalyptus oil with a possible range at or between 0.001%-2%, Myrrh with a possible range at or between 0.001%-2%, Plant Extract (strawberry extract) with a possible range at or between 0.001%-2%, Other essential oils with a possible range at or between 0.001%-2%, Hydroxyapatite with a possible range at or between 0.001% -20%, Green tea extract with a possible range at or between 0.001%-2%, Tea tree oil with a possible range at or between 0.001%-2% and Grapefruit Seed Extract with a possible range at or between 0.001%-2%.

Another embodiment of the present invention may include the following ingredients separated into different components that are later mixed right before use. The first component could include the ozonated oil with calcium and 0.09% peroxide (hydrogen peroxide) and various fillers. The second side could include all the other various ingredients including the fluoride and phosphate and other active ingredients. The present invention uses all natural ingredients, natural fluoride, calcium citrate and zinc, magnesium chloride, baking soda and peroxide.

Another embodiment of the present invention may include various combination of items. For example ozonated oil with essential oils such as Eucalyptol at 0.09%, Mentol at 0.04%, Thymol at 0.06% or with Aloe Vera Oil or the Co enzyme Q 10 or with the proteolytic enzymes such as papain or bromelain or with the zinc chloride or with the probiotic. The embodiments without the flouride should at least contain chlorhexidine at about 0.2% in the rinse and 2% in the toothpaste.

The present invention may also include the following ingredients: Aloe Vera, Vitamin E, Ozonated oil (probably Ozonated Olive oil), Proteoltic enzymes (probably papain from papaya fruit and Bromelain from pineapple), Xylitol, Sodium Bicarbonate, *Mentha Piperita* (Peppermint) Oil, *Prunus Spinosa* (Blackthorn) Fruit Juice, *Commiphora Myrrha* (Myrrh) Extract, *Krameria Triandra* (Ratanhia) Root Extract, *Aesculus Hippocastanum* (Horse Chestnut) Bark Extract, *Arum Maculatum* Root Extract, Sodium Chloride (Salt), Cyanopsis Tetragonoloba (Guar) Gum, *Simmondsia Chinensis* (Jojoba) Seed Oil, Esculin, Limonene, Linalool.eucalyptus oil, myrrh, plant extract (strawberry extract), and essential oils, hydroxylapatite, Co enzyme Q 10, Green tea extract, Tea tree oil, grapefruit seed extract, Probiotics, Cranberry powder, Vitamins.

FIG. 1 illustrates a front view of an exemplary embodiment of the product container 10 of the present invention. This product container 10 has a multitude of chambers/cavities all integrated into a single container structure. A first chamber 12 contains either the oxidative composition or the reductant composition. The second chamber 14 contains the other of the oxidative composition or the reductant composition. The pump 16 is configured to be manually pressed or pressurized and will release both the oxidative and reductant compositions together such that the two compositions can work together during brushing.

Integrated at the bottom of the container 10 is a third chamber 18 and a fourth chamber 20. These chambers/cavities (18, 20) are accessible through a cap 22. The cap 22 can be a rubber cap that seals the chambers 18, 20. Alternatively, the cap 22 may be a variety of cap-like structures made from polymers, rubbers or synthetic material. Inside the chambers can be stored the probiotic lozenges as earlier described. Furthermore, the other chamber can store probiotic gums or even test strips. For instance, a thiol test strip or equivalent sulfur test strip can be stored in one of the chambers such that the user can test for bad breath.

This particular container allows for the seamless use of the present invention. The user can dispense the final composition of the oxidative and reductant mixture for brushing. This will effectively clean the mouth. Then the user can use a probiotic lozenge to install the new and healthy bacteria that promote a clean mouth until the next cleaning. By integrating these chambers/cavities all into one container 10 the user is less likely to forget a step or lose an essential component of the oral care system.

Although several embodiments have been described in detail for purposes of illustration, various modifications may be made to each without departing from the scope and spirit of the invention. Accordingly, the invention is not to be limited, except as by the appended claims.

What is claimed is:

1. A probiotic formulation, comprising:
   i.) *lactobacillus acidophilus* comprising 15.0% to 40.0% per mass of the probiotic formulation;
   ii.) *lactobacillus reuteri* comprising 5.0% to 20.0% per mass of the probiotic formulation;
   iii.) *lactobacillus salivarius* comprising 5.0% to 20.0% per mass of the probiotic formulation;
   iv.) *lactobacillus paracasei* comprising 5.0% to 20.0% per mass of the probiotic formulation;
   v.) *streptococcus* thermophiles comprising 5.0% to 20.0% per mass of the probiotic formulation;
   vi.) *streptococcus salivarius* BLIS K-12 comprising 5.0% to 30.0% per mass of the probiotic formulation;
   vii.) *streptococcus salivarius* BLIS M-18 comprising 5.0% to 30.0% per mass of the probiotic formulation;
   viii.) zinc oxide comprising 0.2% to 5.0% per mass of the probiotic formulation;
   ix.) hydroxyapatite comprising 0.1% to 25.0% per mass of the probiotic formulation; and
   x.) dicalcium phosphate comprising 0.1% to 5.0% per mass of the probiotic formulation.

2. The formulation of claim 1, wherein the probiotic formulation further includes *lactobacillus brevis* comprising 5.0% to 20.0% per mass of the probiotic formulation.

3. The formulation of claim 1, wherein the formulation comprises a lozenge.

4. The formulation of claim 1, wherein the formulation comprises a gum.

5. The formulation of claim 1, wherein after a first cleaning the formulation is insertable within a user's mouth installing new and healthy bacteria promoting a clean mouth until a second cleaning.

6. A probiotic formulation, comprising:
   i.) *lactobacillus acidophilus* comprising 15.0% to 40.0% per mass of the probiotic formulation;
   ii.) *lactobacillus reuteri* comprising 5.0% to 20.0% per mass of the probiotic formulation;
   iii.) *lactobacillus salivarius* comprising 5.0% to 20.0% per mass of the probiotic formulation;
   iv.) *lactobacillus paracasei* comprising 5.0% to 20.0% per mass of the probiotic formulation;
   v.) *streptococcus* thermophiles comprising 5.0% to 20.0% per mass of the probiotic formulation;
   vi.) *streptococcus salivarius* BLIS K-12 comprising 5.0% to 30.0% per mass of the probiotic formulation;
   vii.) *streptococcus salivarius* BLIS M-18 comprising 5.0% to 30.0% per mass of the probiotic formulation;
   viii.) zinc oxide comprising 0.2% to 5.0% per mass of the probiotic formulation; and
   ix.) dicalcium phosphate comprising 0.1% to 5.0% per mass of the probiotic formulation.

7. The formulation of claim 6, wherein the probiotic formulation further includes hydroxyapatite comprising 0.1% to 25.0% per mass of the probiotic formulation.

8. The formulation of claim 6, wherein the probiotic formulation further includes *lactobacillus brevis* comprising 5.0% to 20.0% per mass of the probiotic formulation.

9. The formulation of claim 6, wherein the formulation comprises a lozenge.

10. The formulation of claim 6, wherein the formulation comprises a gum.

11. The formulation of claim 6, wherein after a first cleaning the formulation is insertable within a user's mouth installing new and healthy bacteria promoting a clean mouth until a second cleaning.

12. A probiotic formulation, comprising:
    i.) *lactobacillus acidophilus* comprising 15.0% to 40.0% per mass of the probiotic formulation;
    ii.) *lactobacillus reuteri* comprising 5.0% to 20.0% per mass of the probiotic formulation;
    iii.) *lactobacillus salivarius* comprising 5.0% to 20.0% per mass of the probiotic formulation;
    iv.) *lactobacillus paracasei* comprising 5.0% to 20.0% per mass of the probiotic formulation;
    v.) *streptococcus* thermophiles comprising 5.0% to 20.0% per mass of the probiotic formulation;
    vi.) *streptococcus salivarius* BLIS K-12 comprising 5.0% to 30.0% per mass of the probiotic formulation;
    vii.) *streptococcus salivarius* BLIS M-18 comprising 5.0% to 30.0% per mass of the probiotic formulation; and
    viii.) zinc oxide comprising 0.2% to 5.0% per mass of the probiotic formulation.

13. The formulation of claim 12, wherein the probiotic formulation further includes dicalcium phosphate comprising 0.1% to 5.0% per mass of the probiotic formulation.

14. The formulation of claim 12, wherein the probiotic formulation further includes hydroxyapatite comprising 0.1% to 25.0% per mass of the probiotic formulation.

15. The formulation of claim 12, wherein the probiotic formulation further includes *lactobacillus brevis* comprising 5.0% to 20.0% per mass of the probiotic formulation.

16. The formulation of claim 12, wherein the formulation comprises a lozenge.

17. The formulation of claim 12, wherein the formulation comprises a gum.

18. The formulation of claim 12, wherein after a first cleaning the formulation is insertable within a user's mouth installing new and healthy bacteria promoting a clean mouth until a second cleaning.

* * * * *